US005674735A

United States Patent [19]

Onions et al.

[11] Patent Number: 5,674,735

[45] Date of Patent: Oct. 7, 1997

[54] DNA ENCODING THE EHV-4 GH OR GC GLYCOPROTEIN

[75] Inventors: David Edward Onions; Lesley Nicolson, both of Glasgow, United Kingdom

[73] Assignees: University Court of the University of Glasgow, Glasgow; Equine Virology Research Foundation, Suffolk, both of United Kingdom

[21] Appl. No.: 344,536

[22] Filed: Nov. 23, 1994

Related U.S. Application Data

[63] Continuation of Ser. No. 961,672, May 6, 1993, abandoned.

[30] Foreign Application Priority Data

Jul. 6, 1990 [GB] United Kingdom .................... 9014950

[51] Int. Cl.$^6$ ............................ C12N 15/63; C12N 15/86; C12N 15/38

[52] U.S. Cl. ................ 435/252.3; 435/69.3; 435/252.33; 435/254.11; 435/254.2; 435/320.1; 536/23.72

[58] Field of Search ................................ 435/69.3, 252.3, 435/320.1, 252.33, 254.11, 254.2; 536/23.72

[56] References Cited

U.S. PATENT DOCUMENTS 4,769,330 9/1988 Paoletti .
4,879,213 11/1989 Fox et al. .
5,338,683 8/1994 Paoletti et al. .

FOREIGN PATENT DOCUMENTS

WO 90/01546 2/1990 WIPO .

OTHER PUBLICATIONS

A.A. Cullinane et al., *J. Gen. Virol* 69, 1575–1590 (1988). "Characterization of the genome of equine herpesvirus 1 subtype 2".

P. Guo et al. *Journal of Virology*, 63, 4189–4198 (1989). "Expression in Recombinant Vaccinia Virus of the Equine Herpesvirus 1 Gene Encoding Glycoprotein gp13 and Protection of Immunized Animals".

Chowdhury et al. Virus Research 11(2): 127–139(see abstract) 1988.

Lee et al. Science 239:1288–1291 1988.

Stern. Tibtech 9:163–167 1991.

Bowie et al. Science 247:1306 1990.

Young and Davis PNAS 80: 1194–1198 1983.

Grunstein PNAS 72(10): 3961 1975.

Sambrook, Laboratory Manual 1989 see Chapter 12; pp. 12.1–12.40.

Hopp and Woods PNAS 78:3824 1981.

*Primary Examiner*—Anthony C. Caputa
*Attorney, Agent, or Firm*—Bell, Seltzer, Park & Gibson

[57] ABSTRACT

The present invention involves isolated nucleic acid molecules encoding the equine herpesvirus-4 (EHV-4) gH or gC polypeptide, the polypeptides so encoded, and antigenic fragments thereof. Vectors and host cells containing these nucleic acid sequences, and uses thereof, are presented.

12 Claims, 2 Drawing Sheets

DNA ENCODING THE EHV-4 GH OR GC GLYCOPROTEIN

RELATED APPLICATIONS

This is a continuation of application Ser. No. 07/961,672, filed on May 6, 199, now abandoned, which is the national phase of PCT/GB91/01091, Jul. 4, 1991.

FIELD OF THE INVENTION

The present invention is concerned with a nucleic acid sequence encoding an Equine herpesvirus-4 polypeptide, a recombinant nucleic acid molecule comprising such a nucleic acid sequence, a vector virus or host cell containing said nucleic acid sequence, an EHV-4 polypeptide, antibodies immuno-reactive with said polypeptide, a vaccine against EHV-4 infection, as well as methods for the preparation of such a vaccine.

BACKGROUND OF THE INVENTION

Equine herpesvirus-4 (EMV-4) is, like the related equine herpesvirus-1, an alphaherpesvirus responsible for significant economic losses within the equine industry. EHV-4 is primarily associated with respiratory disease though EMV-4 induced abortions are occasionally reported.

The genome of EHV-4 has been characterized as a double-stranded linear DNA molecule consisting of two covalently linked segments (L, 109 kbp; S, 35 kbp) the latter being flanked by inverted repeats.

The glycoproteins of herpesviruses mediate essential viral functions such as cellular attachment, penetration into cells and pathogenicity. Furthermore, herpesvirus glycoproteins are critical components in the interaction of the virus with the host immune system.

SUMMARY OF THE INVENTION

A first aspect of the present invention is a nucleic acid sequence encoding EHV-4 gH or gC polypeptide, or an antigenic fragment thereof.

A second aspect of the present invention is a nucleic acid sequence encoding a polypeptide having an amino acid sequence of SEQ ID NO:4 or SEQ ID NO:2, or an antigenic fragments thereof.

A further aspect of the present invention is a nucleic acid sequence selected from the group of SEQ ID NO:1, SEQ ID NO:3, and fragments of these sequences which encode polypeptides having EHV-gH or EHV-gC antigenicity.

A further aspect of the present invention is an EHV-4 gH or gC polypeptide or an antigenic fragment thereof.

DETAILED DESCRIPTION OF THE INVENTION

Figure 1:
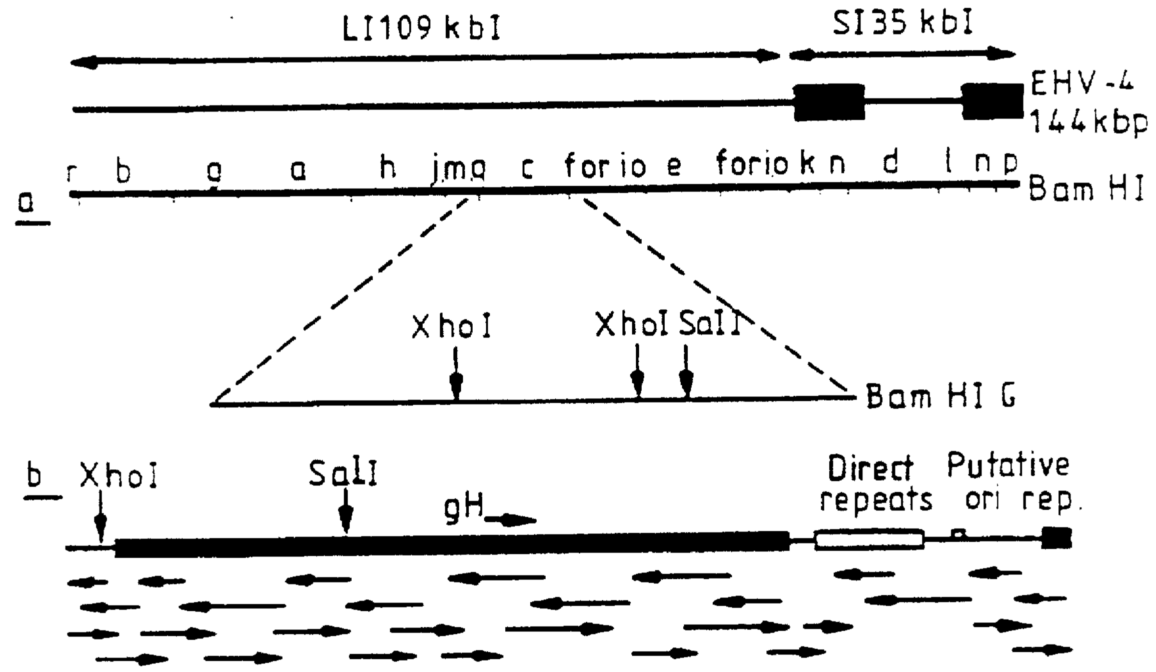
FIG. 1A shows the BamHI restriction map of the EHV-4 genome (Cullinane A. A. et al., *J. Gen. Virol.*, 69:1575 (1988).
FIG. 1B shows the sequencing strategy and localization of the EHV-4 gH gene.

A number of studies, predominantly with the well-characterized glycoproteins of herpes simplex virus (HSV), have demonstrated the importance of herpesvirus glycoproteins in both antibody and cellular immune responses.

Although considerable diversity exists among the herpesvirus glycoproteins in structure and function, some similarities in DNA and protein sequence have been identified. This has led to the classification of several herpesvirus proteins into different groups, each consisting of homologous proteins being related by the presence of specific conserved regions or sites. Groups of such homologues are for example: Herpes Simplex virus-1 (HSV-1) gB, Pseudorabies virus (PRV) gII, Bovine herpesvirus (BHV) gI; HSV-1, gD, PRV gp50, BHV gIV; EHV-1 gp14, PRV gI, Varicella-zoster virus (VZV) gII.

The gH proteins of Herpes simplex virus type 1, *Varicella-zoster* virus and Pseudorabies virus (PRV) have been mapped and sequenced and showned to be involved in protection against the virus (Gompels, U. and A. Minson (1986), Virology 153, 230; Keller, P. M. et al. (1987), Virology 157, 526; Patent application WO 89/10965). gC-type glycoprotein sequences of several herpesviruses have been published, e.g. HSV-1, PRV, EHV-1 (Frink, R. J. et al. (1983), J. Virol. 45, 634; Robbins, A. K. et al. (1986), J. Virol. 58, 339; Allen, G. P. and Coogle, L. D. (1988), J. Virol. 62, 2850).

However, none of these documents disclose the characterization or exact localisation of the EHV-4 gH or gC homologue on the EHV-4 genome nor do they disclose or teach the use of said proteins or genes encoding said proteins for the preparations of a vaccine to prevent EHV-4 infection.

Herein, the EHV-4 gH-type protein and gC-type protein are termed EHV-4 gH and EHV-4 gC, respectively.

Control by vaccination of EHV-4 infection has been a long-sought goal.

Current vaccines comprise chemically inactivated virus vaccines and modified live-virus vaccines. However, inactivated vaccines generally induce only a low level of immunity, requiring additional immunizations, disadvantageously require adjuvants and are expensive to produce. Further, some infectious virus particles may survive the inactivation process and causes disease after administration to the animal.

In general, attenuated live virus vaccines are preferred because they evoke a more long-lasting immune response (often both humoral and cellular) and are easier to produce. Up to now, only live attenuated EHV-4 vaccines are available which are based on live EHV-4 virus attenuated by serial passages of virulent strains in tissue culture. However, because of this treatment uncontrolled mutations are introduced into the viral genome, resulting in a population of virus particles heterogeneous in their virulence and immunizing properties In addition it is well known that such traditional attenuated live virus vaccines can revert to virulence resulting in disease of the inoculated animals and the possible spread of the pathogen to other animals.

Vaccines containing only the necessary and relevant EHV-4 immunogenic material which is capable of eliciting an immune response against the pathogen, or genetic information encoding said material, do not display above-mentioned disadvantages of the live or inactivated vaccines.

According to the present invention a nucleic acid sequence encoding EHV-4 gH or gC polypeptide, or an antigenic fragment thereof can be applied for the preparation of a vaccine for the immunization of horses against EHV-4 infection which does not display above-mentioned drawbacks of inactivated or live attenuated vaccines.

"Nucleic acid sequence" as used herein refers to a polymeric form of nucleotides of any length, both to ribonucleic acid sequences and to deoxy-ribonucleic acid sequences. In principle, this term refers to the primary structure of the molecule. Thus, this term includes double and single stranded DNA, as well as double and single stranded RNA, and modifications thereof. In general, the term "polypeptide" refers to a molecular chain of amino acid with a biological activity, does not refer to a specific length of the product and if required can be modified in vivo or in vitro, for example by glycosylation, amidation, carboxylation or phosphorylation; thus inter alia peptides, oligopeptides and proteins are included.

Said gH or gC polypeptide are homologous with their gH or gC counter-parts of other herpesviruses and can be identified and characterized by the conserved regions and sites within the gH or gC polypeptide homologues.

The gene encoding EHV-4 gH polypeptide maps to the BamHI C fragment (FIG. 1) and encodes a protein of 855 amino acids in length with a predicted molecular weight of 94.100 D. From the amino acid sequence (SEQ ID NO: 2) the following structural features characteristic of membrane glycoproteins can be derived:

A signal peptide within the extreme N-terminal region of the primary translation product comprising a stretch of hydrophobic amino acid residues is identified. The cleavage site is at about $Ala_{19}$, the predicted molecular weight of gH after cleavage of the signal peptide being about 92.130 D.

Residues 20–816 constitute the hydrophilic external domain which possesses 11 N-linked glycosylation sites (N-X-S/T).

The hydrophobic transmembrane domain of about 20 amino acid residues is located towards the C terminus at about position 837–855.

The cytoplasmic domain of EHV-4 gH stretches from about amino acid position 837–855.

A comparison of the amino sequence of the gH proteins of alpha, beta and gamma herpesviruses by Gompels et al. (J. Gen. Virol. 69, 2819, 1988) and Cranage et al. (J. Virol. 62, 1416, 1988) highlighted several features of the gH protein conserved throughout the herpesvirus family an unusually short cytoplasmic domain of 14 or 15 amino acids in alphaherpesviruses and of 7 or 8 amino acids in beta and gammaherpesviruses four conserved cysteine residues at similar positions relative to the putative transmembrane domain and within conserved local sequence, and a conserved glycosylation site sequence NGTV 13–18 amino acids N-terminal to the transmembrane domain. EHV-4 gH exhibits all above features: the proposed cytoplasmic domain is under 20 amino acids in length, the four conserved cysteines are present at positions 556, 591, 663 and 716, and the C-terminal glycosylation site is located within the sequence NGTV (amino acids 796–799) which is positioned 19 amino acids N-terminal to the putative EHV-4 transmembrane domain. The Cys residues at 737 and 740 in the EHV-4 gH occur at sites of cysteine conservation throughout most herpesvirus gHs, with the exception of HSV-1. The strong conservation of cysteine residues between the EHV-4 and HSV-1 gHs and, indeed, throughout the alpha, beta and gammaherpesvirus gHs investigated implies some degree of conservation of the secondary and tertiary structure of these proteins presumably involving disulphide bonding (Gompels et al., 1988, ibid).

The gene encoding the EHV-4 gC polypeptide maps to the BamHI G fragment (FIG. 2) and encodes a protein of 485 amino acids in length with a molecular weight of about 52.500 D. From the amino acid sequence (SEQ ID NO: 4) the following structural features characteristic of membrane glycoproteins can be derived:

The signal peptide is identified at the N-terminus spanning about 32 amino acids with cleavage occuring between the Ala and Ser residues at positions 32 and 33 respectively The external domain of EHV-4 gC spans about residues 33 to 444 and possesses 11 N-linked glycosylation sites (N-X-S/T).

An antigenic determinant of EHV-4 gC is located at about residue 409 (Asn) (Hopp and Woods (1981), PNAS 78, 3824).

Amino acids 445–468 constitute the glycoprotein transmembrane domain.

The C-terminal cytoplasmic domain spans residues 469 to 485, is hydrophilic and possesses a net positive charge of 2.

gC homologues comprise inter alia conserved amino acids in the C-terminal half positioned around six sites of cysteine conservation. A few of the N-linked glycosylation sites exist in similar positions but are not strictly conserved. A further common feature of gCs is that the C-terminal cytoplasmic domain is short and positively charged (Fitzpatrick, D. R. et al. (1989), Virology 173, 46; Allen, G. P. and Coogle, L. D., ibid).

For the purpose of comparing the EHV-4 gC to other gCs in terms of the specifically conserved features an alignment of EHV-4 gC, BHV-1 gIII, PRV gIII, HSV-1 gC, and MDV A antigen is carried out. EHV-4 gC possesses cysteine residues at each of the six conserved positions, amino acids 256, 318, 357, 361, 390 and 416. Nine putative EHV-4 gC glycosylation sites are conserved in EHV-1 gp13 and three in PRY gIII.

Also included within the present invention are nucleic acid sequences encoding an antigenic fragment of the EHV-4 gH or gC polypeptide, i.e. a fragment of said gH or gC polypeptide comprising a molecular configuration capable of eliciting any type of immune response, humoral and/or cellular, against said gH or gC polypeptide in a susceptible animal, when presented in a suitable form. Furthermore, said fragment is characteristic for an EHV-4 gH or gC polypeptide.

Particularly, a nucleic acid sequence according to the invention can be used that encodes an EHV-4 polypeptide having an amino acid sequence depicted in SEQ ID NO: 1 or SEQ ID NO: 2, or a derivative of said polypeptide.

The gene encoding the EHV-4 gH and gC polypeptide haven been localized on the EHV-4 genome and the nucleotide sequences thereof are depicted in SEQ ID NO: 1 and SEQ ID NO: 3, respectively.

This information can be used to genetically manipulate said genes or derivatives thereof, for example to clone the genes by recombinant DNA techniques generally known in the art and to express the polypeptides encoded thereby in vitro or in vivo. Nucleic acid sequences having abovementioned nucleotide sequences or derivatives thereof are preferably used for the expression of the EHV-4 gH or gC polypeptides.

It will be understood that for the particular EHV-4 gH or gC polypeptide embraced herein, natural variations can exist between individual EHV-4 viruses or strains. These variations may be demonstrated by (an) amino acid difference(s) in the overall sequence or by deletions, substitutions, insertions, inversions or additions of (an) amino acid(s) in said sequence. All such derivatives are included within the scope of this invention. Moreover, the potential exist to use recombinant DNA technology for the preparation of nucleic acid sequences encoding these various derivates.

As is well known in the art, the degeneracy of the genetic code permits substitution of bases in a codon resulting in an other codon but still coding for the same amino acid, e.g. the codon for the amino acid glutamic acid is both GAT and GAA. Consequently, it is clear that for the expression of a polypeptide with the amino acid sequence shown in SEQ ID NO: 2 or SEQ ID NO: 4, or an antigenic fragment thereof use can be made of a derivate nucleic acid sequence with such an alternative codon composition different from the nucleic acid sequence shown in said SEQ ID No:1 and SEQ ID NO:3.

Furthermore, also fragments derived from the EHV-4 gH or gC polypeptide or from the amino acid sequences depicted in SEQ ID NO: 1 or SEQ ID NO: 2 which still display EHV-4 gH or gC antigenic properties, or fragments derived from The nucleotide sequences encoding the EHV-4 gH or gC polypeptide or derived from the nucleotide sequences depicted in said SEQ ID NO: 1 and SEQ ID NO:3 encoding antigenic fragments of said gH or gC polypeptides are also included in the present invention.

All such modifications mentioned above resulting in such derivatives of the EHV-4 gH or gC polypeptide or gene are covered by the present invention so long as the characteristic EHV-4 gH Or gC features remain unaffected in essence.

A nucleic acid sequence according to the present invention can be ligated to various expression effecting DNA sequences, optionally containing portions of DNA encoding fusion protein sequences such as β-galactosidase, resulting in a so called recombinant nucleic acid molecule which can be used for the transformation of a suitable host. Such hybrid DNA molecules, are preferably derived from, for example plasmids, or from nucleic acid sequences present in bacteriophages or viruses.

Specific vectors which can be used to clone nucleic acid sequences according to the invention are known in the art (e.g. Rodriguez, R. L. and D. T. Denhardt, edit., Vectors: A survey of molecular cloning vectors and their uses, Butterworths, 1988).

The methods to be used for the construction of a recombinant nucleic acid molecule according to the invention are know to those of ordinary skill in the art and are inter alia set forth in Maniatis, T. et al. (Molecular Cloning: A Laboratory Manual, Cold Spring Harbor Laboratory, 1982).

"Transformation", as used herein, refers to the introduction of a heterologous nucleic acid sequence into a host cell, irrespective of the method used, for example direct uptake or transduction. The heterologous nucleic acid sequence may be maintained through autonomous replication or alternatively, may be integrated into the host genome. The recombinant DNA molecules preferably are provided with appropriate control sequences compatible with the designated host which can regulate the expression of the inserted nucleic acid sequence.

A suitable host cell is a cell which can be transformed by a nucleic acid sequence encoding a polypeptide or by a recombinant nucleic acid molecule comprising such a nucleic acid sequence and which can be used to express said polypeptide coded by said nucleic acid sequence. The host cell can be of procaryotic origin, e.g. bacteria such as *E. coli, B. subtilis* and Pseudomonas species; or of eucaryotic origin such as yeasts, e.g *Saccharomyces cerevisiae* or higher eucaryotic cells such as insect, plant or mammalian cells, including HeLa cells and Chinese hamster ovary (CHO) cells. Insect cells include the Sf9 cell line of *Spodoptera frigiperda*. Information with respect to the cloning and expression of the nucleic acid sequences of the present invention in eucaryotic cloning systems can be found in Esser, K. et al. (Plasmids of Eukaryotes, Springer-Verlag, 1986).

The nucleic acid sequences of the present invention are preferably operably linked to expression control sequences.

Such control sequences may comprise promoters, operators, inducers, ribosome binding sites etc.

When the host cells are bacteria, illustrative useful expression control sequences include the trp promoter and operator (Goeddel, et al., Nucl. Acids Res. 8, 4057, 1980); the lac promoter and operator (Chang, et al., Nature 275, 615, 1978); the outer membrane protein promoter (EMBO J. 1, 771–775, 1982); the bacteriophage λ promoters and operators (Nucl. Acids Res. 11, 4677–4688, 1983); the α-amylase (*B. subtilis*) promoter and operator, termination sequences and other expression enhancement and control sequences compatible with the selected host cell. When the host cell is yeast, illustrative useful expression control sequences include, e.g., α-mating factor. For insect cells the polyhedrin promoter of baculoviruses can be used (Mol. Cell. Biol. 3, 2156–65, 1983). When the host cell is of insect or mammalian origin illustrative useful expression control sequences include, e.g., the SV-40 promoter (Science 222, 524–527, 1983) or, e.g., the metallothionein promoter (Nature 296, 39–42, 1982) or a heat shock promoter (Voellmy et al., Proc. Natl. Acad. Sci. U.S.A. 82, 4949–53, 1985).

Alternatively, also expression control sequence present in EHV-4, in particular those regulating the expression of gH or gC may be applied.

The present invention also comprises an EHV-4 gH or gC polypeptide or an antigenic fragment thereof, essentially free from the whole virus or other protein with which it is ordinarily associated.

In particular, a polypeptide comprising at least part of the amino acid sequence depicted in SEQ ID NO: 1 or SEQ ID NO: 2 or derivatives thereof is included in the present invention.

In an other embodiment of the invention a polypeptide having an amino acid sequence encoded by a nucleic acid sequence mentioned above is used.

Immunization of horses against EHV-4 infection can, for example be achieved by administering to the horse a polypeptide according to the invention as a so-called subunit vaccine. The subunit vaccine according to the invention may comprise a polypeptide in a pure form, optionally in the presence of a pharmaceutically acceptable carrier. The polypeptide can optionally be covalently bonded to a non-related protein, which, for example can be of advantage in the purification of the fusion product. Examples are β-galactosidase, protein A, prochymosine, blood clotting factor Xa, etc.

In some cases the ability to raise neutralizing antibodies against these polypeptides per se may be low. Small fragments are preferably conjugated to carrier molecules in order to raise their immunogenicity. Suitable carriers for this purpose are macromolecules, such as natural polymers (proteins, like key hole limpet hemocyanin, albumin, toxins), synthetic polymers like polyamino acids (polylysine, polyalanine), or micelles of amphiphilic compounds like saponins. Alternatively these fragments may be provided as polymers thereof, preferably linear polymers.

Polypeptides to be used in such subunit vaccines can be prepared by methods known in the art, e.g. by isolation said polypeptides from EHV-4, by recombinant DNA techniques or by chemical synthesis.

If required the polypeptides according to the invention to be used in a vaccine can be modified in vitro or in vivo, for example by glycosylation, amidation, carboxylation or phosphorylation.

An alternative to subunit vaccines are live vector vaccines. A nucleic acid sequence according to the invention is introduced by recombinant DNA techniques into a micro-organism (e.g. a bacterium or virus) in such a way that the recombinant micro-organism is still able to replicate thereby expressing a polypeptide coded by the inserted nucleic acid sequence. Next, this recombinant micro-organism can be administered to the horse for immunization whereafter it maintains itself for some time, or even replicates, in the body of the inoculated horse, expressing in vivo a polypeptide coded for by the inserted nucleic acid sequence according to the invention resulting in the stimulation of the immune system of the inoculated horse. Suitable vectors for the incorporation of a nucleic acid sequence according to the invention are derived from, for example viruses such as EHV-1, adenovirus, vaccinia virus or other pox viruses, papilloma virus or bacteria such as *E. coli* or specific Salmonella species. With recombinant micro-organisms of this type, the polypeptide synthesized in the host cell can be exposed as a surface antigen. In this context fusion of the said polypeptide with OMP proteins or pilus proteins of *Escherichia coli* or synthetic provision of signal and anchor sequences which are recognized by the organism are conceivable. It is also possible that the said immunogenic polypeptide, if desired as part of a larger whole, is released inside the animal to be immunized. In all of these cases it is also possible that one or more immunogenic products will find expression which generate protection against various pathogens and/or against various antigens of a given pathogen.

A vaccine according to the invention can be prepared by culturing a host cell comprising a nucleic acid sequence according to the invention, whereafter the cells and/or vector viruses grown in the cells can be collected, optionally in a pure form, and formed to a vaccine optionally in a lyophilized form.

Abovementioned host cells comprising a nucleic acid sequence according to the invention can also be cultured under conditions which are favourable for the expression of a polypeptide coded by said nucleic acid sequence. Vaccines may be prepared using samples of the crude culture, host cell lysates or host cell extracts, although in another embodiment more purified polypeptides according to the invention are formed to a vaccine, depending on its intended use. In order to purify the polypeptides produced, host cells containing a nucleic acid sequence according to the invention are cultured in an adequate volume and the polypeptides produced are isolated from such cells or from the medium if the protein is excreted. Polypeptides excreted into the medium can be isolated and purified by standard techniques, e.g. salt fractionation, chromatography, centrifugation, whereas intracellular polypeptides can be isolated by first collecting said cells, lysing the cells followed by separation of the polylpeptides from the other intracellular components and forming the polypeptides to a vaccine.

It goes without saying that horses already infected by EHV-4 can be treated with antibodies directed against said EHV-4. Antiserum or antibodies characteristic for a polypeptide according to the invention can be used for the therapeutic treatment of EHV-4 infection. Said characteristic antiserum or antibodies may be obtained by immunizing animals with an effective amount of EHV-4 gH or gC polypeptide in order to elicit an appropriate immune response. Thereafter the animals are bled and antiserum can be prepared.

Monoclonal antibodies directed against a polypeptide according to the invention can also be used for the therapy of horses infected with EHV-4. Said monoclonal antibodies can be produced by methods known in the art for this purpose, e.g. by immunizing mice with said polypeptide, immortalizing mouse spleen cells and selecting hybridomas producing useful antibodies. Immortal antibody-producing cell lines can also be created by direct transformation of B lymphocytes with oncogenic DNA, or transfection with Epstein-Barr virus.

Monoclonal antibodies, in particular, may be used to raise anti-idiotype antibodies by methods known in the art. These anti-idiotype antibodies may also be useful for prevention of EHV-4 infection in horses.

Abovementioned antiserum and monoclonal antibodies can also be used for the immunological diagnosis of horses infected with EHV-4.

The vaccine according to the invention can be administered in a conventional active immunization scheme: single or repeated administration in a manner compatible with the dosage formulation and in such amount as will be prophylactically and/or therapeutically effective and immunogenic. The administration of the vaccine can be done, e.g. intradermally, subcutaneously, intramusculary, intravenously or intranasally.

Additionally the vaccine may also contain an aqueous medium or a water containing suspension, often mixed with other constituents, e.g. in order to increase the activity and/or shelf life. These constituents may be salts, pH buffers, stabilizers (such as skimmed milk or casein hydrolysate), emulsifiers, adjuvants to improve the immune response (e.g. oils, muramyl dipeptide, aluminium hydroxide, saponin, polyanions and amphipatic substances) and preservatives.

It is clear that a vaccine according to the invention may also contain immunogens related to other pathogens of horses or may contain nucleic acid sequences encoding these immunogens, like antigens of EHV-1, equine influenza virus, -rotavirus, -infectious anemia virus, -arteritis virus, -encephalitis virus, Borna disease virus of horses, Berue virus of horses, *E. coli* or *Streptococcus equi* to produce a multivalent vaccine.

EXAMPLE 1

Isolation and characterization of gH gene.

1. Culturing of EHV-4 virus

Roller bottles of slightly sub-confluent monolayers of equine dermal cells (NBL-6) grown in Earle's Minimum Essential Medium (Flow) supplemented with 0,2% sodium bicarbonate, 1% non-essential amino acids, 1% glutamine, 100 units/ml penicillin, 100 mg/ml streptomycin and 10% foetal calf serum were infected with virus of the EHV-4 strain 1942 at a m.o.i. of 0,003 and allowed to adsorb for 60 min at 37° C. They were incubated at 31° C. unitil extensive c.p.e. was evident and the majority of cells had detached from the bottle surface (2–6 days). The infected cell medium was centrifuged at 5.000 r.p.m. for 5 min to pellet the cells, and the supernatant was centrifuged at 12.000 r.p.m. for 2 hours in a Sorvall GSA 6×200 ml rotor. The pellet was resuspended in 5 ml PBS, sonicated and centrifuged at 11.000 r.p.m. in a Sorvall SS34 rotor for 5 min to spin down cellular debris. Virus was then pelleted by centrifugation at 18.000 r.p.m. in a Sorvall SS34 rotor for 1 hour. Ratios of virus particles to plaque-forming units were approximately 1.000 to 5.000.

2. Preparation of EHV-4 DNA

The pelleted virus was resuspended in 10 ml NTE (NaCl/Tris/EDTA) and briefly sonicated. Contaminating cellular DNA was degraded by adding DNase at 10 μg/ml and incubating at 37° C. for 1 hour. SDS was added to a final concentration of 2%, and the preparation was extracted approximately 3 times with NTE equilibrated phenol until a clear interphase was obtained.

A chloroform extraction was followed by ethanol precipitation of the DNA as described above. The DNA was pelleted, washed with 70% ethanol, resuspended in 10 ml of 100 mM NaCl and 10 μg/ml RNase and left overnight at room temperature. Further purification was achieved by treatment with 1 mg/ml proteinase K for 2 hours at 31° C. The DNA was extracted once with phenol:chloroform (1:1 vol/vol), once with chloroform, ethanol precipitated, drained well and resuspended in 0.1×SSC.

3. Cloning of EHV-4 DNA

EHV-4 BamHI DNA fragments were ligated into the vector pUC9, a plasmid which includes the ampicillin-resistance gene from pBR322 and the polylinker region from M13mp9 (Vieira, J. and Messing, J. (1982), Gene 19, 259). 5 μg of EHV-4 DNA and 5 μg pUC9 DNA were separately digested with BamHI.

Complete digestion was verified by gel electrophoresis of aliguots of the reactions and then the DNA was extracted twice with an equal volume of phenol:chloroform (1:1) and ethanol-precipitated. Ligation was performed essentially by the method of Tanaka and Weisblum (J. Bact. 121, 354, 1975). Approximately 0.1 μg of BamHI digested pUC9 and 1 μg of BamHI-digested EHV-4 DNA were mixed in 50 mM Tris-HCl pH 7.5, 8 mM $MgCl_2$, 10 mM dithiothreitol, 1 mM ATP in a final volume of 40 μl. 2 units of T4 DNA ligase (0.5 μl) were then added. The reaction was incubated at 4° C. for 16 hours.

Calcium-shocked *E.coli* DHI cells (Hanahan, D. (1983), J. Mol. Biol. 166, 557) were transformed with the recombinant plasmids essentially described by Cohen et al. (Proc. Natl. Acad. Sci., U.S.A. 69, 2110, 1972). Additional clones were derived by restriction digestion of recombinant plasmid pUC9 containing BamHI C fragment (FIG. 1), followed by recovering of the specific EHV-4 restriction fragments and sub-cloning thereof (Maniatis, T. et al., ibid) within the multi-cloning site of the Bluescript M13+ plasmid vector (Stratagene) for sequence analysis.

The nucleotide sequence of a region of BamHI C fragment spanning the gH gene was determined by using single stranded plasmid DNA as template and Bluescript-derived and custom-made oligonucleotides as primers in a Sanger dideoxy sequencing strategy (Sanger et al., Proc. Natl. Acad. Sci 74, 5463, 1977) (FIG. 1). The exact localisation, nucleic acid sequence and corresponding amino acid sequence of the gH gene is shown in the SEQ ID NO: 1 and SEQ ID NO: 2, respectively.

EXAMPLE 2

Isolation and characterization of gC gene.

Culturing of EHV-4 virus, preparation of EHV-4 DNA and construction of a BamHI library in pUC9 was carried out as outlined above.

Recombinant plasmid pUC9:EHV-4 BamHI G was restriction enzyme digested to generate subfragments of EHV-4 BamHI G which were then isolated from 0.7% agarose gels and cloned into a Bluescript M13+ plasmid vector (Stratagene) by standard techniques (Maniatis, T. et al., ibid.). Recombinant plasmids were propagated in *E. coli* strain JM83 in l-broth supplemented with ampicillin (100 μg/ml). Plasmid DNA was extracted from 500 ml bacterial cultures by the alkaline lysis method and purified by banding on CsCl gradients.

DNA sequencing was carried out by the Sanger dideoxy technique (Sanger et al., ibid.) using denatured recombinant plasmid DNA as template and M13+-specific or custom oligonucleotides as primers.

Figure 2:
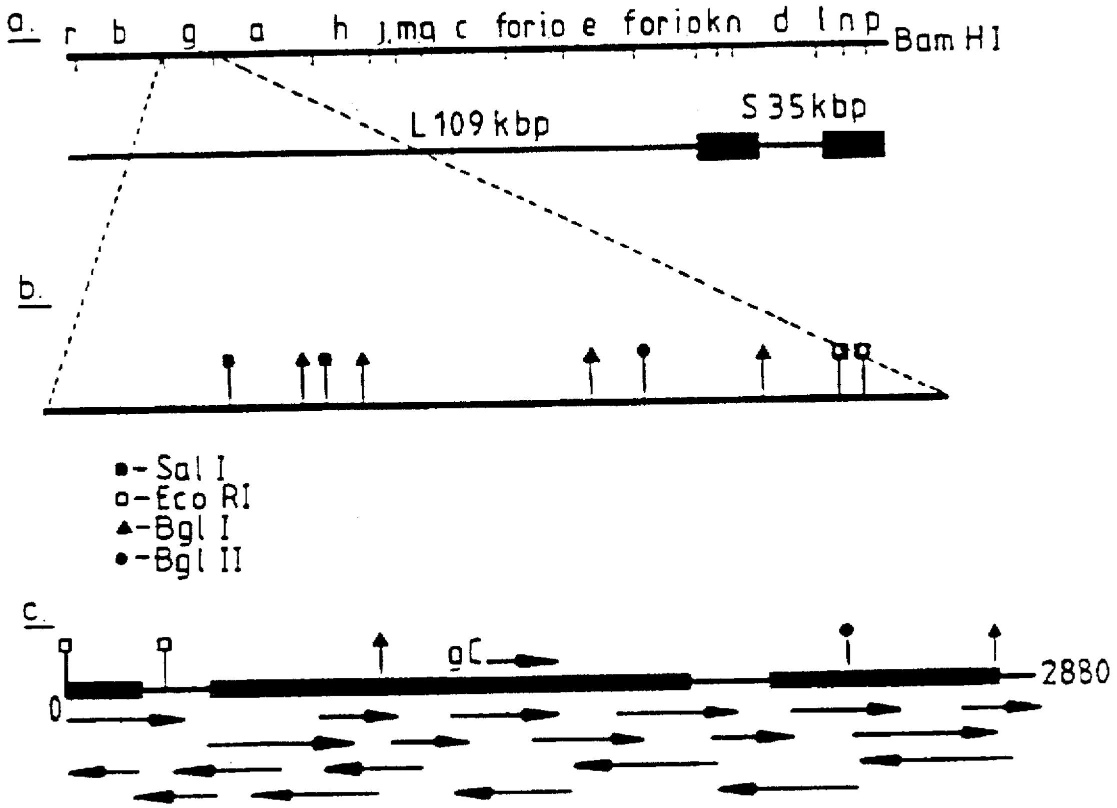
FIG. 2A shows the BamHI restriction map of the EHV-4 genome (Cullinane A. A. et al., *J. Gen. Virol.*, 69:1575 (1988).
FIG. 2B shows the restriction map of Bam HI G indicating sites of cleavage of SalI, EcoRI, BglI and BglII.
FIG. 2C shows the sequencing strategy and limits of open reading frames within the BamHI G fragment.

The nucleotide sequence of a region of the BamHI G fragment spanning the gC gene was determined by analysis of overlapping sequences according to the strategy detailed in FIG. 2.

The exact localisation, nucleotide sequence and corresponding amino acid sequence of the gC gene is shown in the SEQ ID NO: 3 and SEQ ID NO: 4, respectively.

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 2730 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 65..2629

( x i ) SEQUENCE DESCRIPTION: SEQ ID NO:1:

```
CAGCGCGGCC GAGATACTCG AGGTATCCAG TGGTTGTATA TTGGGAATAA ATACTGCTGC        60

GATT ATG TCA CAA CCG TAT CTA AAA ATA GCT ATC TTA GTG GCC GCT ACT        109
     Met Ser Gln Pro Tyr Leu Lys Ile Ala Ile Leu Val Ala Ala Thr
       1               5                  10                  15
```

-continued

ATT GTG TCT GCG ATT CCC GTT TGG ACA ACA CCG GTT TCA ACT TCA CCA 157
Ile Val Ser Ala Ile Pro Val Trp Thr Thr Pro Val Ser Thr Ser Pro
20 25 30

CCC CAA CAA ACA AAA TTG CAC TAT GTG GGA AAT GGT ACC TGG GTA CAC 205
Pro Gln Gln Thr Lys Leu His Tyr Val Gly Asn Gly Thr Trp Val His
35 40 45

AAC AAT ACA TTC AAC GTA ACC AGG TAT GAC AGG ATA ACC ATG GAA CCA 253
Asn Asn Thr Phe Asn Val Thr Arg Tyr Asp Arg Ile Thr Met Glu Pro
50 55 60

GTT TAT AAT AAC AAT TTA TCC TCT ACT ACC TTT TTT GTT GCT ATA TCG 301
Val Tyr Asn Asn Asn Leu Ser Ser Thr Thr Phe Phe Val Ala Ile Ser
65 70 75

GAG AGA AAT TTT CGC ACG GTT AAC ACT CCA CTT GGA GCG TCC GTA TTT 349
Glu Arg Asn Phe Arg Thr Val Asn Thr Pro Leu Gly Ala Ser Val Phe
80 85 90 95

TGG ATT TTA AAA AGC GCT CTT AAT CCT CCC AAA CAC CAA CCC TGT ATA 397
Trp Ile Leu Lys Ser Ala Leu Asn Pro Pro Lys His Gln Pro Cys Ile
100 105 110

GCT AAT GTG CCA GAA CCC GGT GAC CCA CGC GGA CCG TGC GTC AAC TCA 445
Ala Asn Val Pro Glu Pro Gly Asp Pro Arg Gly Pro Cys Val Asn Ser
115 120 125

ACT GTG AGT CTA TTT TTT AAT GAC AAT TTG GAG CCG TTT TTA ATG ACA 493
Thr Val Ser Leu Phe Phe Asn Asp Asn Leu Glu Pro Phe Leu Met Thr
130 135 140

AAA AAT CTT TTG GAG TTT GAA GTA TTG CCC GAC AAC TAC ATA ACC GGA 541
Lys Asn Leu Leu Glu Phe Glu Val Leu Pro Asp Asn Tyr Ile Thr Gly
145 150 155

TGG ACG TTT GAG CGG TCT AAA ACT GTG GCT ACG AAA GGC AAC CCG GTT 589
Trp Thr Phe Glu Arg Ser Lys Thr Val Ala Thr Lys Gly Asn Pro Val
160 165 170 175

GGA GTG GTT CTC TCC CCT CCC CGA ACA AGT CCG GAT GTA AAT AAC ACC 637
Gly Val Val Leu Ser Pro Pro Arg Thr Ser Pro Asp Val Asn Asn Thr
180 185 190

ATA AGA GAT GAT GGC ACC CCT AAA CAG CAC TTG AGC ATT ATA GAC GAA 685
Ile Arg Asp Asp Gly Thr Pro Lys Gln His Leu Ser Ile Ile Asp Glu
195 200 205

CAT ACT ACG TTC GTG CTC GAC CTG CAA AAT TTT ACA AAA ACT TTA ACT 733
His Thr Thr Phe Val Leu Asp Leu Gln Asn Phe Thr Lys Thr Leu Thr
210 215 220

TAT ATA AGC CCA TTT GCT GCG GTG TGG CCA ATA ACA GCC TTT CAT GCC 781
Tyr Ile Ser Pro Phe Ala Ala Val Trp Pro Ile Thr Ala Phe His Ala
225 230 235

GGA ATT ACA GTA ATG GGG TGT GAC ACA ACT CAG GCG ATT GCG TAC CTC 829
Gly Ile Thr Val Met Gly Cys Asp Thr Thr Gln Ala Ile Ala Tyr Leu
240 245 250 255

GGC AAT GGG TTT ATG GGT TTG CAA ATA AGC TCG GTA AAC AAT CCA CCG 877
Gly Asn Gly Phe Met Gly Leu Gln Ile Ser Ser Val Asn Asn Pro Pro
260 265 270

CTG GAG ATG ATT GTT GCA CCA AAT GAC GTC CGT GCT CGG ATA GTT AAC 925
Leu Glu Met Ile Val Ala Pro Asn Asp Val Arg Ala Arg Ile Val Asn
275 280 285

CGC CTT CCC CCA AGA CGT CGA CTT GAG CCA CCC GGG CCA TAT GCA GGA 973
Arg Leu Pro Pro Arg Arg Arg Leu Glu Pro Pro Gly Pro Tyr Ala Gly
290 295 300

CCT ATC TAC AAG GTG TAC GTA CTC AGT GAT GGA AAT TTT TAC TTG GGT 1021
Pro Ile Tyr Lys Val Tyr Val Leu Ser Asp Gly Asn Phe Tyr Leu Gly
305 310 315

CAT GGC ATG AGC AAG ATT TCT AGG GAG GTT GCC GCG TAC CCA GAA GAG 1069
His Gly Met Ser Lys Ile Ser Arg Glu Val Ala Ala Tyr Pro Glu Glu
320 325 330 335

-continued

| | | | | | | | | | | | | | | | | |
|---|---|---|---|---|---|---|---|---|---|---|---|---|---|---|---|---|
| AGT | TTG | GAC | TAC | CGC | TAC | CAC | TTA | TCG | CTT | GCC | AAC | CTT | GAT | ACT | CTG | 1117 |
| Ser | Leu | Asp | Tyr | Arg | Tyr | His | Leu | Ser | Leu | Ala | Asn | Leu | Asp | Thr | Leu | |
| | | | | 340 | | | | | 345 | | | | | 350 | | |
| GCT | ATG | TTG | GCA | GAA | CTT | TCT | TCC | GGT | AAG | AGC | AAG | GAT | GTG | AGC | TAT | 1165 |
| Ala | Met | Leu | Ala | Glu | Leu | Ser | Ser | Gly | Lys | Ser | Lys | Asp | Val | Ser | Tyr | |
| | | | 355 | | | | | 360 | | | | | 365 | | | |
| TAC | TTG | TAT | CGC | ATA | ATT | GCG | AGG | CTG | GCC | GTA | GCA | ACG | TTT | TCC | CTT | 1213 |
| Tyr | Leu | Tyr | Arg | Ile | Ile | Ala | Arg | Leu | Ala | Val | Ala | Thr | Phe | Ser | Leu | |
| | | 370 | | | | | 375 | | | | | 380 | | | | |
| GCA | GAA | GTT | ATA | CGC | CTG | AGT | GAC | TAT | ATG | CTC | CTT | CAA | GAG | GCC | ATC | 1261 |
| Ala | Glu | Val | Ile | Arg | Leu | Ser | Asp | Tyr | Met | Leu | Leu | Gln | Glu | Ala | Ile | |
| | 385 | | | | | 390 | | | | | 395 | | | | | |
| GAC | GTG | GAT | ATA | AAC | CTC | CGC | CTA | ATT | GTA | CCT | CTA | GTG | ATG | AAG | TAC | 1309 |
| Asp | Val | Asp | Ile | Asn | Leu | Arg | Leu | Ile | Val | Pro | Leu | Val | Met | Lys | Tyr | |
| 400 | | | | | 405 | | | | | 410 | | | | | 415 | |
| GCC | GCT | GGG | GGA | ACG | GCA | GAT | AGC | TCG | TAC | ACA | TCC | TCG | GAC | GTA | GCT | 1357 |
| Ala | Ala | Gly | Gly | Thr | Ala | Asp | Ser | Ser | Tyr | Thr | Ser | Ser | Asp | Val | Ala | |
| | | | | 420 | | | | | 425 | | | | | 430 | | |
| ATG | GAC | CAA | TTC | GAG | GTG | GCT | CAA | GCC | CAG | ATT | GAG | AAG | ATA | GTA | GCC | 1405 |
| Met | Asp | Gln | Phe | Glu | Val | Ala | Gln | Ala | Gln | Ile | Glu | Lys | Ile | Val | Ala | |
| | | | 435 | | | | | 440 | | | | | 445 | | | |
| GAT | ATA | AAT | ATC | GAA | AAT | GAA | TTG | CGC | AAA | CCT | ATG | TAC | GAG | CAC | CGC | 1453 |
| Asp | Ile | Asn | Ile | Glu | Asn | Glu | Leu | Arg | Lys | Pro | Met | Tyr | Glu | His | Arg | |
| | | 450 | | | | | 455 | | | | | 460 | | | | |
| TCA | TTA | TTG | AAA | AGC | GTG | TAC | GCT | TAT | TCT | AGA | AAG | CCG | CTA | CCA | AAC | 1501 |
| Ser | Leu | Leu | Lys | Ser | Val | Tyr | Ala | Tyr | Ser | Arg | Lys | Pro | Leu | Pro | Asn | |
| | 465 | | | | | 470 | | | | | 475 | | | | | |
| GCG | GTA | AGC | TTT | GCT | AAC | CGG | CTC | ATC | ACG | GCT | ATG | TAT | AAA | GAA | GCA | 1549 |
| Ala | Val | Ser | Phe | Ala | Asn | Arg | Leu | Ile | Thr | Ala | Met | Tyr | Lys | Glu | Ala | |
| 480 | | | | | 485 | | | | | 490 | | | | | 495 | |
| ATT | AAG | GAC | AGA | ATT | ACG | TGG | AAC | TCT | ACG | ATG | CGA | GAG | GTG | TTA | TTT | 1597 |
| Ile | Lys | Asp | Arg | Ile | Thr | Trp | Asn | Ser | Thr | Met | Arg | Glu | Val | Leu | Phe | |
| | | | | 500 | | | | | 505 | | | | | 510 | | |
| TTT | GCG | GTT | GGT | GCT | GCT | GCA | GGT | TCG | CAT | GTT | ATC | CTC | ACG | GAT | GGG | 1645 |
| Phe | Ala | Val | Gly | Ala | Ala | Ala | Gly | Ser | His | Val | Ile | Leu | Thr | Asp | Gly | |
| | | | 515 | | | | | 520 | | | | | 525 | | | |
| CCA | GAT | CTC | GGT | TTA | CAT | GCC | CAC | AAA | GAT | TCT | TCG | ATG | TTT | CTA | TCT | 1693 |
| Pro | Asp | Leu | Gly | Leu | His | Ala | His | Lys | Asp | Ser | Ser | Met | Phe | Leu | Ser | |
| | | 530 | | | | | 535 | | | | | 540 | | | | |
| CTT | AAC | CGC | AAC | ATA | CTC | TTG | TTG | TGT | ACG | GCC | ATG | TGT | ACG | GCG | TCG | 1741 |
| Leu | Asn | Arg | Asn | Ile | Leu | Leu | Leu | Cys | Thr | Ala | Met | Cys | Thr | Ala | Ser | |
| | 545 | | | | | 550 | | | | | 555 | | | | | |
| CAT | GCC | GTG | TCC | GCA | GGA | GTA | AAA | CTA | GAG | GAA | GTT | ATG | GCT | GGC | CTT | 1789 |
| His | Ala | Val | Ser | Ala | Gly | Val | Lys | Leu | Glu | Glu | Val | Met | Ala | Gly | Leu | |
| 560 | | | | | 565 | | | | | 570 | | | | | 575 | |
| ATT | GCC | GGG | GGT | GTA | CAA | TTT | AGC | CTC | CTA | GAA | GTA | TTT | AGT | CCA | TGT | 1837 |
| Ile | Ala | Gly | Gly | Val | Gln | Phe | Ser | Leu | Leu | Glu | Val | Phe | Ser | Pro | Cys | |
| | | | | 580 | | | | | 585 | | | | | 590 | | |
| ATG | GCG | TCT | GCT | CGA | TTT | GAC | CTG | GCC | GAA | GAA | GAG | CAT | GTG | CTA | GAT | 1885 |
| Met | Ala | Ser | Ala | Arg | Phe | Asp | Leu | Ala | Glu | Glu | Glu | His | Val | Leu | Asp | |
| | | | 595 | | | | | 600 | | | | | 605 | | | |
| CTA | CTG | TCC | GTT | ATC | CCA | CCT | CGC | CTG | TAC | ACC | GAC | TTA | AAC | ACT | GGC | 1933 |
| Leu | Leu | Ser | Val | Ile | Pro | Pro | Arg | Leu | Tyr | Thr | Asp | Leu | Asn | Thr | Gly | |
| | | 610 | | | | | 615 | | | | | 620 | | | | |
| TTG | GAG | GAC | GAC | GGA | ACC | ACC | ATC | CAT | TCA | TAC | GGA | CGG | TCT | GCT | AAC | 1981 |
| Leu | Glu | Asp | Asp | Gly | Thr | Thr | Ile | His | Ser | Tyr | Gly | Arg | Ser | Ala | Asn | |
| | 625 | | | | | 630 | | | | | 635 | | | | | |
| GGA | ATT | TTA | AAC | TCT | CGA | ATC | GCA | TAT | AAC | TTT | GAT | GCT | GTT | CGT | GTA | 2029 |
| Gly | Ile | Leu | Asn | Ser | Arg | Ile | Ala | Tyr | Asn | Phe | Asp | Ala | Val | Arg | Val | |
| 640 | | | | | 645 | | | | | 650 | | | | | 655 | |

-continued

```
TTT ACT CCA GAG TTG GCC TCA TGC AGC ACT AAA CTA CCA AAA GTT TTG      2077
Phe Thr Pro Glu Leu Ala Ser Cys Ser Thr Lys Leu Pro Lys Val Leu
                660                 665                 670

GTA GTG CTA CCC TTA GCA TCA AAC CGA AGC TAC GTT ATA ACT CGT ACT      2125
Val Val Leu Pro Leu Ala Ser Asn Arg Ser Tyr Val Ile Thr Arg Thr
            675                 680                 685

GCG CCC AAT ATA GGT TTA ACT TAC TCT CTT GAT GGG GTA AAT ATA GCA      2173
Ala Pro Asn Ile Gly Leu Thr Tyr Ser Leu Asp Gly Val Asn Ile Ala
        690                 695                 700

AAG CCT ATA GTC ATC AGT TAC ATC ACT TAT GGA AAT TGT CAA GTT TCG      2221
Lys Pro Ile Val Ile Ser Tyr Ile Thr Tyr Gly Asn Cys Gln Val Ser
    705                 710                 715

AGA GCT ACA ATC AGG TCA GTT TAC TTG GAC CAT CCG GGC CAC ACC CAG      2269
Arg Ala Thr Ile Arg Ser Val Tyr Leu Asp His Pro Gly His Thr Gln
720                 725                 730                 735

TCG TGC GTA TAT TGC GGG AGT GTG TTT ATG CGG TAT ATG GCA TCC GGA      2317
Ser Cys Val Tyr Cys Gly Ser Val Phe Met Arg Tyr Met Ala Ser Gly
                740                 745                 750

GCA ATT ATG GAT TTG ATA TAC ATA GAT GAC AAA GAT GTA GAG TTG CAA      2365
Ala Ile Met Asp Leu Ile Tyr Ile Asp Asp Lys Asp Val Glu Leu Gln
            755                 760                 765

CTG GTA GCA GGG GAA AAC TCA ACT ATT CCA GCC TTT AAC CCA AAG CTG      2413
Leu Val Ala Gly Glu Asn Ser Thr Ile Pro Ala Phe Asn Pro Lys Leu
        770                 775                 780

TAT ACG CCC AGC ATG AAT GCT CTT TTA ATG TTT CCA AAC GGA ACA GTA      2461
Tyr Thr Pro Ser Met Asn Ala Leu Leu Met Phe Pro Asn Gly Thr Val
    785                 790                 795

ACC CTA ATG TCT GCA TTT GCA TCC TAC TCA GCT TTT AAA ATT CCC AGT      2509
Thr Leu Met Ser Ala Phe Ala Ser Tyr Ser Ala Phe Lys Ile Pro Ser
800                 805                 810                 815

ACT TAT CTG TGG GCT TCT ATT GGG GGT TTG TTG CTG GCT ATT CTG ATT      2557
Thr Tyr Leu Trp Ala Ser Ile Gly Gly Leu Leu Leu Ala Ile Leu Ile
                820                 825                 830

TTA TAT GTA ATC GTT AAA ATG TTA TGT GGT GGT GTA ATT AAT AAT GAC      2605
Leu Tyr Val Ile Val Lys Met Leu Cys Gly Gly Val Ile Asn Asn Asp
            835                 840                 845

TAT AGT TTG TTA TTA AAC TCT GAG TAAACACAAA CAATGTCTAG TGTGTTGTAT     2659
Tyr Ser Leu Leu Leu Asn Ser Glu
        850                 855

TGCGTGTAAA CAGTATACGA GTGAACATTT ATACGTAAAA TGGTTAAATT TTATTTTCGC     2719

TATAAACGGG A                                                         2730
```

( 2 ) INFORMATION FOR SEQ ID NO:2:

( i ) SEQUENCE CHARACTERISTICS:
( A ) LENGTH: 855 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met Ser Gln Pro Tyr Leu Lys Ile Ala Ile Leu Val Ala Ala Thr Ile
 1               5                  10                  15

Val Ser Ala Ile Pro Val Trp Thr Thr Pro Val Ser Thr Ser Pro Pro
            20                  25                  30

Gln Gln Thr Lys Leu His Tyr Val Gly Asn Gly Thr Trp Val His Asn
        35                  40                  45

Asn Thr Phe Asn Val Thr Arg Tyr Asp Arg Ile Thr Met Glu Pro Val
    50                  55                  60
```

-continued

| | | | | | | | | | | | | | | | |
|---|---|---|---|---|---|---|---|---|---|---|---|---|---|---|---|
| Tyr | Asn | Asn | Asn | Leu | Ser | Ser | Thr | Thr | Phe | Phe | Val | Ala | Ile | Ser | Glu |
| 65 | | | | | 70 | | | | | 75 | | | | | 80 |
| Arg | Asn | Phe | Arg | Thr | Val | Asn | Thr | Pro | Leu | Gly | Ala | Ser | Val | Phe | Trp |
| | | | | 85 | | | | | 90 | | | | | 95 | |
| Ile | Leu | Lys | Ser | Ala | Leu | Asn | Pro | Pro | Lys | His | Gln | Pro | Cys | Ile | Ala |
| | | | 100 | | | | | 105 | | | | | 110 | | |
| Asn | Val | Pro | Glu | Pro | Gly | Asp | Pro | Arg | Gly | Pro | Cys | Val | Asn | Ser | Thr |
| | | 115 | | | | | 120 | | | | | 125 | | | |
| Val | Ser | Leu | Phe | Phe | Asn | Asp | Asn | Leu | Glu | Pro | Phe | Leu | Met | Thr | Lys |
| | 130 | | | | | 135 | | | | | 140 | | | | |
| Asn | Leu | Leu | Glu | Phe | Glu | Val | Leu | Pro | Asp | Asn | Tyr | Ile | Thr | Gly | Trp |
| 145 | | | | | 150 | | | | | 155 | | | | | 160 |
| Thr | Phe | Glu | Arg | Ser | Lys | Thr | Val | Ala | Thr | Lys | Gly | Asn | Pro | Val | Gly |
| | | | | 165 | | | | | 170 | | | | | 175 | |
| Val | Val | Leu | Ser | Pro | Pro | Arg | Thr | Ser | Pro | Asp | Val | Asn | Asn | Thr | Ile |
| | | | 180 | | | | | 185 | | | | | 190 | | |
| Arg | Asp | Asp | Gly | Thr | Pro | Lys | Gln | His | Leu | Ser | Ile | Ile | Asp | Glu | His |
| | | 195 | | | | | 200 | | | | | 205 | | | |
| Thr | Thr | Phe | Val | Leu | Asp | Leu | Gln | Asn | Phe | Thr | Lys | Thr | Leu | Thr | Tyr |
| | 210 | | | | | 215 | | | | | 220 | | | | |
| Ile | Ser | Pro | Phe | Ala | Ala | Val | Trp | Pro | Ile | Thr | Ala | Phe | His | Ala | Gly |
| 225 | | | | | 230 | | | | | 235 | | | | | 240 |
| Ile | Thr | Val | Met | Gly | Cys | Asp | Thr | Thr | Gln | Ala | Ile | Ala | Tyr | Leu | Gly |
| | | | | 245 | | | | | 250 | | | | | 255 | |
| Asn | Gly | Phe | Met | Gly | Leu | Gln | Ile | Ser | Ser | Val | Asn | Asn | Pro | Pro | Leu |
| | | | 260 | | | | | 265 | | | | | 270 | | |
| Glu | Met | Ile | Val | Ala | Pro | Asn | Asp | Val | Arg | Ala | Arg | Ile | Val | Asn | Arg |
| | | 275 | | | | | 280 | | | | | 285 | | | |
| Leu | Pro | Pro | Arg | Arg | Arg | Leu | Glu | Pro | Pro | Gly | Pro | Tyr | Ala | Gly | Pro |
| | 290 | | | | | 295 | | | | | 300 | | | | |
| Ile | Tyr | Lys | Val | Tyr | Val | Leu | Ser | Asp | Gly | Asn | Phe | Tyr | Leu | Gly | His |
| 305 | | | | | 310 | | | | | 315 | | | | | 320 |
| Gly | Met | Ser | Lys | Ile | Ser | Arg | Glu | Val | Ala | Ala | Tyr | Pro | Glu | Glu | Ser |
| | | | | 325 | | | | | 330 | | | | | 335 | |
| Leu | Asp | Tyr | Arg | Tyr | His | Leu | Ser | Leu | Ala | Asn | Leu | Asp | Thr | Leu | Ala |
| | | | 340 | | | | | 345 | | | | | 350 | | |
| Met | Leu | Ala | Glu | Leu | Ser | Ser | Gly | Lys | Ser | Lys | Asp | Val | Ser | Tyr | Tyr |
| | | 355 | | | | | 360 | | | | | 365 | | | |
| Leu | Tyr | Arg | Ile | Ile | Ala | Arg | Leu | Ala | Val | Ala | Thr | Phe | Ser | Leu | Ala |
| | 370 | | | | | 375 | | | | | 380 | | | | |
| Glu | Val | Ile | Arg | Leu | Ser | Asp | Tyr | Met | Leu | Leu | Gln | Glu | Ala | Ile | Asp |
| 385 | | | | | 390 | | | | | 395 | | | | | 400 |
| Val | Asp | Ile | Asn | Leu | Arg | Leu | Ile | Val | Pro | Leu | Val | Met | Lys | Tyr | Ala |
| | | | | 405 | | | | | 410 | | | | | 415 | |
| Ala | Gly | Gly | Thr | Ala | Asp | Ser | Ser | Tyr | Thr | Ser | Ser | Asp | Val | Ala | Met |
| | | | 420 | | | | | 425 | | | | | 430 | | |
| Asp | Gln | Phe | Glu | Val | Ala | Gln | Ala | Gln | Ile | Glu | Lys | Ile | Val | Ala | Asp |
| | | 435 | | | | | 440 | | | | | 445 | | | |
| Ile | Asn | Ile | Glu | Asn | Glu | Leu | Arg | Lys | Pro | Met | Tyr | Glu | His | Arg | Ser |
| | 450 | | | | | 455 | | | | | 460 | | | | |
| Leu | Leu | Lys | Ser | Val | Tyr | Ala | Tyr | Ser | Arg | Lys | Pro | Leu | Pro | Asn | Ala |
| 465 | | | | | 470 | | | | | 475 | | | | | 480 |
| Val | Ser | Phe | Ala | Asn | Arg | Leu | Ile | Thr | Ala | Met | Tyr | Lys | Glu | Ala | Ile |

-continued 485 490 495

Lys Asp Arg Ile Thr Trp Asn Ser Thr Met Arg Glu Val Leu Phe Phe
500 505 510

Ala Val Gly Ala Ala Ala Gly Ser His Val Ile Leu Thr Asp Gly Pro
515 520 525

Asp Leu Gly Leu His Ala His Lys Asp Ser Ser Met Phe Leu Ser Leu
530 535 540

Asn Arg Asn Ile Leu Leu Leu Cys Thr Ala Met Cys Thr Ala Ser His
545 550 555 560

Ala Val Ser Ala Gly Val Lys Leu Glu Glu Val Met Ala Gly Leu Ile
565 570 575

Ala Gly Gly Val Gln Phe Ser Leu Leu Glu Val Phe Ser Pro Cys Met
580 585 590

Ala Ser Ala Arg Phe Asp Leu Ala Glu Glu Glu His Val Leu Asp Leu
595 600 605

Leu Ser Val Ile Pro Pro Arg Leu Tyr Thr Asp Leu Asn Thr Gly Leu
610 615 620

Glu Asp Asp Gly Thr Thr Ile His Ser Tyr Gly Arg Ser Ala Asn Gly
625 630 635 640

Ile Leu Asn Ser Arg Ile Ala Tyr Asn Phe Asp Ala Val Arg Val Phe
645 650 655

Thr Pro Glu Leu Ala Ser Cys Ser Thr Lys Leu Pro Lys Val Leu Val
660 665 670

Val Leu Pro Leu Ala Ser Asn Arg Ser Tyr Val Ile Thr Arg Thr Ala
675 680 685

Pro Asn Ile Gly Leu Thr Tyr Ser Leu Asp Gly Val Asn Ile Ala Lys
690 695 700

Pro Ile Val Ile Ser Tyr Ile Thr Tyr Gly Asn Cys Gln Val Ser Arg
705 710 715 720

Ala Thr Ile Arg Ser Val Tyr Leu Asp His Pro Gly His Thr Gln Ser
725 730 735

Cys Val Tyr Cys Gly Ser Val Phe Met Arg Tyr Met Ala Ser Gly Ala
740 745 750

Ile Met Asp Leu Ile Tyr Ile Asp Asp Lys Asp Val Glu Leu Gln Leu
755 760 765

Val Ala Gly Glu Asn Ser Thr Ile Pro Ala Phe Asn Pro Lys Leu Tyr
770 775 780

Thr Pro Ser Met Asn Ala Leu Leu Met Phe Pro Asn Gly Thr Val Thr
785 790 795 800

Leu Met Ser Ala Phe Ala Ser Tyr Ser Ala Phe Lys Ile Pro Ser Thr
805 810 815

Tyr Leu Trp Ala Ser Ile Gly Gly Leu Leu Leu Ala Ile Leu Ile Leu
820 825 830

Tyr Val Ile Val Lys Met Leu Cys Gly Gly Val Ile Asn Asn Asp Tyr
835 840 845

Ser Leu Leu Leu Asn Ser Glu
850 855

( 2 ) INFORMATION FOR SEQ ID NO:3:

( i ) SEQUENCE CHARACTERISTICS:
( A ) LENGTH: 1560 base pairs
( B ) TYPE: nucleic acid
( C ) STRANDEDNESS: single
( D ) TOPOLOGY: linear -continued ( i i ) MOLECULE TYPE: DNA (genomic)

( i x ) FEATURE:
( A ) NAME/KEY: CDS
( B ) LOCATION: 52..1506

( x i ) SEQUENCE DESCRIPTION: SEQ ID NO:3:

AAGAGTTATT ATTGTTCTTT GTGGAAAATC GCAAACATAT AACCCACAGC A ATG GGT 57
Met Gly
1

TTG GTA AAT ATA ATG CGA TTC ATA ACA TTT GCG TAT ATA ATC TGT GGG 105
Leu Val Asn Ile Met Arg Phe Ile Thr Phe Ala Tyr Ile Ile Cys Gly
5 10 15

GGG TTT ATA TTA ACA CGC ACG TCT GGG ACC AGT GCT AGC GCC AGT CCA 153
Gly Phe Ile Leu Thr Arg Thr Ser Gly Thr Ser Ala Ser Ala Ser Pro
20 25 30

GCC ACA CCA ACC ACA AAT ACT GGC GAA GGC ACC AGT TCT CCA GTC ACA 201
Ala Thr Pro Thr Thr Asn Thr Gly Glu Gly Thr Ser Ser Pro Val Thr
35 40 45 50

CCA ACT TAC ACA ACC AGT ACG GAC TCT AAT AAT TCA ACA GCC ACG AAC 249
Pro Thr Tyr Thr Thr Ser Thr Asp Ser Asn Asn Ser Thr Ala Thr Asn
55 60 65

AAC TCA ACC GAT GTA AAC GGC ACC GAA GCT ACA CCA ACG CCG AGT CAC 297
Asn Ser Thr Asp Val Asn Gly Thr Glu Ala Thr Pro Thr Pro Ser His
70 75 80

CCA CAT TCA CAT GAA AAT ACA ATT ACA TGC ACA AAT AGT CTC ATA TCG 345
Pro His Ser His Glu Asn Thr Ile Thr Cys Thr Asn Ser Leu Ile Ser
85 90 95

GTT CCC TAC TAC ACA TCT GTT ACC ATT AAC TGT TCT ACA ACA GTA AGT 393
Val Pro Tyr Tyr Thr Ser Val Thr Ile Asn Cys Ser Thr Thr Val Ser
100 105 110

GTA AAT CAC AGT GAA TAC AGA CTA GAA ATT CAC CTA AAC CAG CGC ACC 441
Val Asn His Ser Glu Tyr Arg Leu Glu Ile His Leu Asn Gln Arg Thr
115 120 125 130

CCA TTT TCA GAC ACG CCT CCT GGT GAC CAA GAA AAC TAT GTT AAC CAC 489
Pro Phe Ser Asp Thr Pro Pro Gly Asp Gln Glu Asn Tyr Val Asn His
135 140 145

AAC GCT ACC AAA GAC CAA ACC CTG CTG TTA TTT TCA ACC GCA CAT TCT 537
Asn Ala Thr Lys Asp Gln Thr Leu Leu Leu Phe Ser Thr Ala His Ser
150 155 160

AGC GCG AAA TCT CGA AGG GTT GGC CAG CTG GGC GTT ATT CCA GAC AGG 585
Ser Ala Lys Ser Arg Arg Val Gly Gln Leu Gly Val Ile Pro Asp Arg
165 170 175

CTA CCT AAG CGT CAA CTG TTC AAC CTC CCG GCC CAC ACG AAC GGT GGT 633
Leu Pro Lys Arg Gln Leu Phe Asn Leu Pro Ala His Thr Asn Gly Gly
180 185 190

ACA AAT TTT CCA CTA AAC ATA AAA TCT ATA GAC TGG CGT ACC GCG GGA 681
Thr Asn Phe Pro Leu Asn Ile Lys Ser Ile Asp Trp Arg Thr Ala Gly
195 200 205 210

GTT TAT GTG TGG TAC TTG TTT GCC AAA AAC GGC TCA CTC ATT AAC AGT 729
Val Tyr Val Trp Tyr Leu Phe Ala Lys Asn Gly Ser Leu Ile Asn Ser
215 220 225

ACC AGC GTT ACC GTG TTA ACG TAC AAC GCA CCC CTA ATG GAC CTC TCC 777
Thr Ser Val Thr Val Leu Thr Tyr Asn Ala Pro Leu Met Asp Leu Ser
230 235 240

GTT CAC CCA AGT TTG AAG GGT GAA AAC CAC AGA GCC GTG TGC GTA GTT 825
Val His Pro Ser Leu Lys Gly Glu Asn His Arg Ala Val Cys Val Val
245 250 255

GCT AGC TAC TTT CCC CAC AAC TCT GTT AAG CTG AGG TGG TAT AAA AAC 873
Ala Ser Tyr Phe Pro His Asn Ser Val Lys Leu Arg Trp Tyr Lys Asn
260 265 270

-continued

GCC AAA GAG GTT GAT TTT ACA AAG TAT GTT ACC AAT GCT TCT AGT GTG 921
Ala Lys Glu Val Asp Phe Thr Lys Tyr Val Thr Asn Ala Ser Ser Val
275 280 285 290

TGG GTG GAT GGT CTC ATC ACT CGC ATC TCG ACT GTA TCA ATC CCA GCT 969
Trp Val Asp Gly Leu Ile Thr Arg Ile Ser Thr Val Ser Ile Pro Ala
295 300 305

GAC CCC GAC GAA GAA TAT CCC CCC AGC CTC CGC TGT AGC ATA GAA TGG 1017
Asp Pro Asp Glu Glu Tyr Pro Pro Ser Leu Arg Cys Ser Ile Glu Trp
310 315 320

TAC AGA GAC GAG GTA TCC TTT TCT CGC ATG GCC AAA GCA GGC ACG CCC 1065
Tyr Arg Asp Glu Val Ser Phe Ser Arg Met Ala Lys Ala Gly Thr Pro
325 330 335

TCT GTG TTC GTG GCC CCA ACC GTG TCC GTA AAC GTT GAA GAT GGT GCA 1113
Ser Val Phe Val Ala Pro Thr Val Ser Val Asn Val Glu Asp Gly Ala
340 345 350

GCA GTT TGT ACG GCA GAA TGT GTA CCT AGC AAC GGA GTG TTT GTA TCG 1161
Ala Val Cys Thr Ala Glu Cys Val Pro Ser Asn Gly Val Phe Val Ser
355 360 365 370

TGG GTC GTT AAC GAC CAT TTA CCG GGG GTC CCA TCA CAA GAC GTA ACA 1209
Trp Val Val Asn Asp His Leu Pro Gly Val Pro Ser Gln Asp Val Thr
375 380 385

ACG GGA GTT TGC TCA AGC CAC CCA GGA TTA GTC AAC ATG CGG AGT AGC 1257
Thr Gly Val Cys Ser Ser His Pro Gly Leu Val Asn Met Arg Ser Ser
390 395 400

AGG CCC CTG TCG GAA GAA AAC GGA GAG CGA GAG TAT AAC TGC ATC ATA 1305
Arg Pro Leu Ser Glu Glu Asn Gly Glu Arg Glu Tyr Asn Cys Ile Ile
405 410 415

GAG GGT TAC CCG GAC GGC CTT CCA ATG TTT TCT GAC AGC GTT GTA TAT 1353
Glu Gly Tyr Pro Asp Gly Leu Pro Met Phe Ser Asp Ser Val Val Tyr
420 425 430

GAT GCA TCC CCT ATT GTT GAG GAC ATG CCC GTT TTA ACT GGC ATC ATC 1401
Asp Ala Ser Pro Ile Val Glu Asp Met Pro Val Leu Thr Gly Ile Ile
435 440 445 450

GCC GTT ACT TGC GGG GCC GCA GCG CTA GCG CTG GTT GTT CTC ATT ACA 1449
Ala Val Thr Cys Gly Ala Ala Ala Leu Ala Leu Val Val Leu Ile Thr
455 460 465

GCC GTT TGT TTT TAC TGC TCA AAA CCC TCG CAG GTG CCG TAC AAG AAA 1497
Ala Val Cys Phe Tyr Cys Ser Lys Pro Ser Gln Val Pro Tyr Lys Lys
470 475 480

GCA GAC TTC TAAGCTCGTC GTCAGTTTGA ACAGCAGCTG GTTTTTTTAA 1546
Ala Asp Phe
485

ATACAGTTCA AACC 1560

( 2 ) INFORMATION FOR SEQ ID NO:4:

( i ) SEQUENCE CHARACTERISTICS:
( A ) LENGTH: 485 amino acids
( B ) TYPE: amino acid
( D ) TOPOLOGY: linear ( i i ) MOLECULE TYPE: protein ( x i ) SEQUENCE DESCRIPTION: SEQ ID NO:4:

Met Gly Leu Val Asn Ile Met Arg Phe Ile Thr Phe Ala Tyr Ile Ile
1 5 10 15

Cys Gly Gly Phe Ile Leu Thr Arg Thr Ser Gly Thr Ser Ala Ser Ala
20 25 30

Ser Pro Ala Thr Pro Thr Thr Asn Thr Gly Glu Gly Thr Ser Ser Pro
35 40 45

Val Thr Pro Thr Tyr Thr Thr Ser Thr Asp Ser Asn Asn Ser Thr Ala

-continued 50 55 60

Thr Asn Asn Ser Thr Asp Val Asn Gly Thr Glu Ala Thr Pro Thr Pro
65 70 75 80

Ser His Pro His Ser His Glu Asn Thr Ile Thr Cys Thr Asn Ser Leu
85 90 95

Ile Ser Val Pro Tyr Tyr Thr Ser Val Thr Ile Asn Cys Ser Thr Thr
100 105 110

Val Ser Val Asn His Ser Glu Tyr Arg Leu Glu Ile His Leu Asn Gln
115 120 125

Arg Thr Pro Phe Ser Asp Thr Pro Pro Gly Asp Gln Glu Asn Tyr Val
130 135 140

Asn His Asn Ala Thr Lys Asp Gln Thr Leu Leu Leu Phe Ser Thr Ala
145 150 155 160

His Ser Ser Ala Lys Ser Arg Arg Val Gly Gln Leu Gly Val Ile Pro
165 170 175

Asp Arg Leu Pro Lys Arg Gln Leu Phe Asn Leu Pro Ala His Thr Asn
180 185 190

Gly Gly Thr Asn Phe Pro Leu Asn Ile Lys Ser Ile Asp Trp Arg Thr
195 200 205

Ala Gly Val Tyr Val Trp Tyr Leu Phe Ala Lys Asn Gly Ser Leu Ile
210 215 220

Asn Ser Thr Ser Val Thr Val Leu Thr Tyr Asn Ala Pro Leu Met Asp
225 230 235 240

Leu Ser Val His Pro Ser Leu Lys Gly Glu Asn His Arg Ala Val Cys
245 250 255

Val Val Ala Ser Tyr Phe Pro His Asn Ser Val Lys Leu Arg Trp Tyr
260 265 270

Lys Asn Ala Lys Glu Val Asp Phe Thr Lys Tyr Val Thr Asn Ala Ser
275 280 285

Ser Val Trp Val Asp Gly Leu Ile Thr Arg Ile Ser Thr Val Ser Ile
290 295 300

Pro Ala Asp Pro Asp Glu Glu Tyr Pro Pro Ser Leu Arg Cys Ser Ile
305 310 315 320

Glu Trp Tyr Arg Asp Glu Val Ser Phe Ser Arg Met Ala Lys Ala Gly
325 330 335

Thr Pro Ser Val Phe Val Ala Pro Thr Val Ser Val Asn Val Glu Asp
340 345 350

Gly Ala Ala Val Cys Thr Ala Glu Cys Val Pro Ser Asn Gly Val Phe
355 360 365

Val Ser Trp Val Val Asn Asp His Leu Pro Gly Val Pro Ser Gln Asp
370 375 380

Val Thr Thr Gly Val Cys Ser Ser His Pro Gly Leu Val Asn Met Arg
385 390 395 400

Ser Ser Arg Pro Leu Ser Glu Glu Asn Gly Glu Arg Glu Tyr Asn Cys
405 410 415

Ile Ile Glu Gly Tyr Pro Asp Gly Leu Pro Met Phe Ser Asp Ser Val
420 425 430

Val Tyr Asp Ala Ser Pro Ile Val Glu Asp Met Pro Val Leu Thr Gly
435 440 445

Ile Ile Ala Val Thr Cys Gly Ala Ala Ala Leu Ala Leu Val Val Leu
450 455 460

Ile Thr Ala Val Cys Phe Tyr Cys Ser Lys Pro Ser Gln Val Pro Tyr
465 470 475 480

-continued

Lys Lys Ala Asp Phe
485

( 2 ) INFORMATION FOR SEQ ID NO:5:

( i ) SEQUENCE CHARACTERISTICS:
( A ) LENGTH: 855 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:5:

Met Ser Glu Pro Tyr Leu Lys Ile Ala Ile Leu Val Ala Ala Thr Ile
1 5 10 15

Val Ser Ala Ile Pro Val Trp Thr Thr Pro Val Ser Thr Ser Pro Pro
20 25 30

Glu Glu Thr Lys Leu His Tyr Val Gly Asn Gly Thr Trp Val His Asn
35 40 45

Asn Thr Phe Asn Val Thr Arg Tyr Asp Arg Ile Thr Met Glu Pro Val
50 55 60

Tyr Asn Asn Asn Leu Ser Ser Thr Thr Phe Phe Val Ala Ile Ser Glu
65 70 75 80

Arg Asn Phe Arg Thr Val Asn Thr Pro Leu Gly Ala Ser Val Phe Trp
85 90 95

Ile Leu Lys Ser Ala Leu Asn Pro Pro Lys His Glu Pro Cys Ile Ala
100 105 110

Asn Val Pro Glu Pro Gly Asp Pro Arg Gly Pro Cys Val Asn Ser Thr
115 120 125

Val Ser Leu Phe Phe Asn Asp Asn Leu Glu Pro Phe Leu Met Thr Lys
130 135 140

Asn Leu Leu Glu Phe Glu Val Leu Pro Asp Asn Tyr Ile Thr Gly Trp
145 150 155 160

Thr Phe Glu Arg Ser Lys Thr Val Ala Thr Lys Gly Asn Pro Val Gly
165 170 175

Val Val Leu Ser Pro Pro Arg Thr Ser Pro Asp Val Asn Asn Thr Ile
180 185 190

Arg Asp Asp Gly Thr Pro Lys Glu His Leu Ser Ile Ile Asp Glu His
195 200 205

Thr Thr Phe Val Leu Asp Leu Gln Asn Phe Thr Lys Thr Leu Thr Tyr
210 215 220

Ile Ser Pro Phe Ala Ala Val Trp Pro Ile Thr Ala Phe His Ala Gly
225 230 235 240

Ile Thr Val Met Gly Cys Asp Thr Thr Glu Ala Ile Ala Tyr Leu Gly
245 250 255

Asn Gly Phe Met Gly Leu Glu Ile Ser Ser Val Asn Asn Pro Pro Leu
260 265 270

Glu Met Ile Val Ala Pro Asn Asp Val Arg Ala Arg Ile Val Asn Arg
275 280 285

Leu Pro Pro Arg Arg Arg Leu Glu Pro Pro Gly Pro Tyr Ala Gly Pro
290 295 300

Ile Tyr Lys Val Tyr Val Leu Ser Asp Gly Asn Phe Tyr Leu Gly His
305 310 315 320

Gly Met Ser Lys Ile Ser Arg Glu Val Ala Ala Tyr Pro Glu Glu Ser
325 330 335

Leu Asp Tyr Arg Tyr His Leu Ser Leu Ala Asn Leu Asp Thr Leu Ala

-continued

| | | | | | | | | | | | | | | | |
|---|---|---|---|---|---|---|---|---|---|---|---|---|---|---|---|
| | | | 340 | | | | | 345 | | | | | 350 | | |
| Met | Leu | Ala | Glu | Leu | Ser | Ser | Gly | Lys | Ser | Lys | Asp | Val | Ser | Tyr | Tyr |
| | | 355 | | | | | 360 | | | | | 365 | | | |
| Leu | Tyr | Arg | Ile | Ile | Ala | Arg | Leu | Ala | Val | Ala | Thr | Phe | Ser | Leu | Ala |
| | 370 | | | | | 375 | | | | | 380 | | | | |
| Glu | Val | Ile | Arg | Leu | Ser | Asp | Tyr | Met | Leu | Leu | Gln | Glu | Ala | Ile | Asp |
| 385 | | | | | 390 | | | | | 395 | | | | | 400 |
| Val | Asp | Ile | Asn | Leu | Arg | Leu | Ile | Val | Pro | Leu | Val | Met | Lys | Tyr | Ala |
| | | | | 405 | | | | | 410 | | | | | 415 | |
| Ala | Gly | Gly | Thr | Ala | Asp | Ser | Ser | Tyr | Thr | Ser | Ser | Asp | Val | Ala | Met |
| | | | 420 | | | | | 425 | | | | | 430 | | |
| Asp | Gln | Phe | Glu | Val | Ala | Gln | Ala | Gln | Ile | Glu | Lys | Ile | Val | Ala | Asp |
| | | 435 | | | | | 440 | | | | | 445 | | | |
| Ile | Asn | Ile | Glu | Asn | Glu | Leu | Arg | Lys | Pro | Met | Tyr | Glu | His | Arg | Ser |
| | 450 | | | | | 455 | | | | | 460 | | | | |
| Leu | Leu | Lys | Ser | Val | Tyr | Ala | Tyr | Ser | Arg | Lys | Pro | Leu | Pro | Asn | Ala |
| 465 | | | | | 470 | | | | | 475 | | | | | 480 |
| Val | Ser | Phe | Ala | Asn | Arg | Leu | Ile | Thr | Ala | Met | Tyr | Lys | Glu | Ala | Ile |
| | | | | 485 | | | | | 490 | | | | | 495 | |
| Lys | Asp | Arg | Ile | Thr | Trp | Asn | Ser | Thr | Met | Arg | Glu | Val | Leu | Phe | Phe |
| | | | 500 | | | | | 505 | | | | | 510 | | |
| Ala | Val | Gly | Ala | Ala | Ala | Gly | Ser | His | Val | Ile | Leu | Thr | Asp | Gly | Pro |
| | | 515 | | | | | 520 | | | | | 525 | | | |
| Asp | Leu | Gly | Leu | His | Ala | His | Lys | Asp | Ser | Ser | Met | Phe | Leu | Ser | Leu |
| | 530 | | | | | 535 | | | | | 540 | | | | |
| Asn | Arg | Asn | Ile | Leu | Leu | Leu | Cys | Thr | Ala | Met | Cys | Thr | Ala | Ser | His |
| 545 | | | | | 550 | | | | | 555 | | | | | 560 |
| Ala | Val | Ser | Ala | Gly | Val | Lys | Leu | Glu | Glu | Val | Met | Ala | Gly | Leu | Ile |
| | | | | 565 | | | | | 570 | | | | | 575 | |
| Ala | Gly | Gly | Val | Gln | Phe | Ser | Leu | Leu | Glu | Val | Phe | Ser | Pro | Cys | Met |
| | | | 580 | | | | | 585 | | | | | 590 | | |
| Ala | Ser | Ala | Arg | Phe | Asp | Leu | Ala | Glu | Glu | Glu | His | Val | Leu | Asp | Leu |
| | | 595 | | | | | 600 | | | | | 605 | | | |
| Leu | Ser | Val | Ile | Pro | Pro | Arg | Leu | Tyr | Thr | Asp | Leu | Asn | Thr | Gly | Leu |
| | 610 | | | | | 615 | | | | | 620 | | | | |
| Glu | Asp | Asp | Gly | Thr | Thr | Ile | His | Ser | Tyr | Gly | Arg | Ser | Ala | Asn | Gly |
| 625 | | | | | 630 | | | | | 635 | | | | | 640 |
| Ile | Leu | Asn | Ser | Arg | Ile | Ala | Tyr | Asn | Phe | Asp | Ala | Val | Arg | Val | Phe |
| | | | | 645 | | | | | 650 | | | | | 655 | |
| Thr | Pro | Glu | Leu | Ala | Ser | Cys | Ser | Thr | Lys | Leu | Pro | Lys | Val | Leu | Val |
| | | | 660 | | | | | 665 | | | | | 670 | | |
| Val | Leu | Pro | Leu | Ala | Ser | Asn | Arg | Ser | Tyr | Val | Ile | Thr | Arg | Thr | Ala |
| | | 675 | | | | | 680 | | | | | 685 | | | |
| Pro | Asn | Ile | Gly | Leu | Thr | Tyr | Ser | Leu | Asp | Gly | Val | Asn | Ile | Ala | Lys |
| | 690 | | | | | 695 | | | | | 700 | | | | |
| Pro | Ile | Val | Ile | Ser | Tyr | Ile | Thr | Tyr | Gly | Asn | Cys | Gln | Val | Ser | Arg |
| 705 | | | | | 710 | | | | | 715 | | | | | 720 |
| Ala | Thr | Ile | Arg | Ser | Val | Tyr | Leu | Asp | His | Pro | Gly | His | Thr | Gln | Ser |
| | | | | 725 | | | | | 730 | | | | | 735 | |
| Cys | Val | Tyr | Cys | Gly | Ser | Val | Phe | Met | Arg | Tyr | Met | Ala | Ser | Gly | Ala |
| | | | 740 | | | | | 745 | | | | | 750 | | |
| Ile | Met | Asp | Leu | Ile | Tyr | Ile | Asp | Asp | Lys | Asp | Val | Glu | Leu | Gln | Leu |
| | | 755 | | | | | 760 | | | | | 765 | | | |

-continued

| | | | | | | | | | | | | | | | |
|---|---|---|---|---|---|---|---|---|---|---|---|---|---|---|---|
| Val | Ala<br>770 | Gly | Glu | Asn | Ser | Thr<br>775 | Ile | Pro | Ala | Phe | Asn<br>780 | Pro | Lys | Leu | Tyr |
| Thr<br>785 | Pro | Ser | Met | Asn | Ala<br>790 | Leu | Leu | Met | Phe | Pro<br>795 | Asn | Gly | Thr | Val | Thr<br>800 |
| Leu | Met | Ser | Ala | Phe<br>805 | Ala | Ser | Tyr | Ser | Ala<br>810 | Phe | Lys | Ile | Pro | Ser<br>815 | Thr |
| Tyr | Leu | Trp | Ala<br>820 | Ser | Ile | Gly | Gly | Leu<br>825 | Leu | Leu | Ala | Ile | Leu<br>830 | Ile | Leu |
| Tyr | Val | Ile<br>835 | Val | Lys | Met | Leu | Cys<br>840 | Gly | Gly | Val | Ile | Asn<br>845 | Asn | Asp | Tyr |
| Ser | Leu<br>850 | Leu | Leu | Asn | Ser | Glu<br>855 | | | | | | | | | |

We claim:

1. An isolated DNA fragment encoding native equine herpes virus-4 glycoprotein H (EHV-4 gH).

2. An isolated DNA fragment encoding a polypeptide having SEQ ID NO:2.

3. An isolated DNA molecule having SEQ ID NO:1.

4. A DNA fragment according to claim 1, wherein said fragment is operably linked to an expression control system.

5. A vector virus containing a DNA fragment according to claim 4.

6. A host cell containing a DNA fragment according to claim 4.

7. An isolated DNA fragment encoding native equine herpes virus-4 glycoprotein C (EHV-4 gC).

8. An isolated DNA fragment according to claim 7 encoding a polypeptide having SEQ ID NO:4.

9. An isolated DNA fragment according to claim 7 having SEQ ID NO:3.

10. A DNA fragment according to claim 7, wherein said fragment is operably linked to an expression control system.

11. A vector virus containing a DNA fragment according to claim 10.

12. A host cell containing a DNA fragment according to claim 10.

* * * * *